US011446662B2

(12) United States Patent  
Sakai et al.

(10) Patent No.: US 11,446,662 B2  
(45) Date of Patent: Sep. 20, 2022

(54) SYSTEM FOR CAPTURING SINGLE CELL-DERIVED BIOMOLECULES

(71) Applicant: Hitachi, Ltd., Tokyo (JP)

(72) Inventors: Tomoyuki Sakai, Tokyo (JP); Masataka Shirai, Tokyo (JP)

(73) Assignee: HITACHI, LTD., Tokyo (JP)

( * ) Notice: Subject to any disclaimer, the term of this patent is extended or adjusted under 35 U.S.C. 154(b) by 151 days.

(21) Appl. No.: 15/762,274

(22) PCT Filed: Mar. 28, 2016

(86) PCT No.: PCT/JP2016/059825  
§ 371 (c)(1),  
(2) Date: Mar. 22, 2018

(87) PCT Pub. No.: WO2017/168493  
PCT Pub. Date: Oct. 5, 2017

(65) Prior Publication Data  
US 2018/0272349 A1 Sep. 27, 2018

(51) Int. Cl.  
*B01L 3/00* (2006.01)  
*C12N 15/10* (2006.01)  
*C12M 1/34* (2006.01)

(52) U.S. Cl.  
CPC ......... *B01L 3/502761* (2013.01); *C12M 1/34* (2013.01); *C12N 15/1013* (2013.01);  
(Continued)

(58) Field of Classification Search  
CPC ....... B01L 3/502761; B01L 2200/0668; B01L 2400/086; B01L 2300/0893;  
(Continued)

(56) References Cited

U.S. PATENT DOCUMENTS

2009/0004730 A1 1/2009 Nitta et al.  
2009/0081773 A1 3/2009 Kaufman  
(Continued)

FOREIGN PATENT DOCUMENTS

JP 2005-521425 A 7/2005  
JP 2008249726 A * 10/2008  
(Continued)

OTHER PUBLICATIONS

The mast cell: Distribution and maturation in the rat, Agents and Actions, D. L. WilhelmL. C. J. YongS.nbsp;G. Watkins (Year: 1978).*

*Primary Examiner* — Benjamin R Whatley  
*Assistant Examiner* — Jean Caraballo-Leon  
(74) *Attorney, Agent, or Firm* — Procopio, Cory, Hargreaves & Savitch LLP

(57) ABSTRACT

A system for capturing a biomolecule in a single cell includes: a two-dimensional array having single cell capture holes on one surface of a substrate, and biomolecule capture areas inside the substrate each comprising a biomolecule capture member for capturing a biomolecule extracted from individual cells respectively captured by the single cell capture holes; a flow channel for flowing a sample containing cells to be assayed, from a 1st direction parallel to the surface of the substrate; a structure on the surface of the substrate and opposed to the 1st direction on the downstream side of each of the single cell capture holes; a 1st application means applying a 1st flow, and a 1st control means; and a 2nd application means applying a 2nd flow orthogonal to the one surface of the substrate toward each biomolecule capture area from each corresponding single cell capture hole, and a 2nd control means.

9 Claims, 12 Drawing Sheets

(52) U.S. Cl.
CPC ............. *B01L 2200/0647* (2013.01); *B01L 2200/0668* (2013.01); *B01L 2300/0819* (2013.01); *B01L 2300/0864* (2013.01); *B01L 2300/0893* (2013.01); *B01L 2400/086* (2013.01)

(58) Field of Classification Search
CPC ..... B01L 2300/0864; B01L 2300/0819; B01L 2200/0647; C12M 1/34; C12N 15/1013
See application file for complete search history.

(56) References Cited

U.S. PATENT DOCUMENTS

| | | | | |
|---|---|---|---|---|
| 2011/0045994 | A1* | 2/2011 | Voldman | G01N 33/5005 506/7 |
| 2012/0244532 | A1* | 9/2012 | Craighead | B01L 3/502761 435/6.11 |
| 2013/0302807 | A1* | 11/2013 | Fowler | C12Q 1/686 435/6.12 |
| 2014/0357511 | A1* | 12/2014 | Handique | G01N 33/57423 506/9 |
| 2015/0268244 | A1* | 9/2015 | Cho | G01N 15/1463 435/7.23 |
| 2015/0299784 | A1* | 10/2015 | Fan | C12N 15/1003 506/26 |
| 2016/0010078 | A1 | 1/2016 | Shirai et al. | |

FOREIGN PATENT DOCUMENTS

| | | | |
|---|---|---|---|
| JP | 2010-539907 A | 12/2010 | |
| JP | 2015-515263 A | 5/2015 | |
| WO | 2003/085379 A2 | 10/2003 | |
| WO | 2006/101051 A1 | 9/2006 | |
| WO | WO-2012017629 A1 * | 2/2012 | ......... G01N 35/0098 |
| WO | 2014/141386 A1 | 9/2014 | |
| WO | 2016/038670 A1 | 3/2016 | |

* cited by examiner (a)

(b)

SYSTEM FOR CAPTURING SINGLE CELL-DERIVED BIOMOLECULES

CROSS-REFERENCE TO RELATED APPLICATIONS

This application is a U.S. National Stage entry of PCT Application No: PCT/JP2016/071139 filed Jul. 19, 2016, which claims priority to Japanese Patent Application No. 2015-106139, filed May 26, 2015, the contents of which are incorporated herein by reference.

TECHNICAL FIELD

The present invention relates to methods for gene expression analysis, cell function analysis, and biological tissue analysis in the fields of disease diagnosis, drug discovery, and the like. Specifically, the present invention relates to a device, a system, and a method for capturing a biomolecule (e.g., mRNA) at a single-cell level and a system and a method for analyzing a biomolecule at a single-cell level.

BACKGROUND ART

In recent years, the importance of analysis with a focus on the difference in genome, gene expression, or protein at a single-cell level upon genome analysis, gene expression analysis, and protein analysis of a biological tissue composed of many cells has started to be recognized. In conventional analyses, analysis for obtaining the standard level of samples has been conducted to analyze biomolecules such as DNAs, RNAs, or proteins extracted from many cells sampled from biological tissues. Therefore, evaluation has been difficult even when the abundance of DNAs, RNAs, or proteins in each cell differs from an average value. Single cell analysis is an important analysis method for solving such problem of averaging.

Single cell analysis is a technique for detecting or quantitatively determining biomolecules in each single cell with high accuracy. In order to carry out single cell analysis, and in particular, analysis of mRNA as a biomolecule, it is necessary to isolate cells in order to treat the cells individually, efficiently extract mRNA to be analyzed from each cell, synthesize cDNA (reverse transcription), and, if necessary, conduct sequence analysis of a product obtained by PCR amplification.

Single cell analysis requires a method for efficiently capturing a biomolecule because a single cell contains a biomolecule (especially mRNA) in a minute amount. In addition, since there are temporal/spatial random variations in the gene expression level in each cell, it is necessary to conduct measurement of many individual cells so as to extract biological/medical parameters as final data based on statistics. Further, as many of reagents used for analysis are expensive substances such as enzymes, it is necessary to reduce the analysis cost by decreasing the amount of a reagent used.

Patent Literature 1 discloses, as means for solving the problem, a single cell analysis device, comprising: a cell capture portion for capturing individual cells; a nucleic acid capture portion formed with DNA-immobilized beads or a porous membrane for capturing nucleic acids, which is arranged under the cell capture portion; and a flow channel that connects the two capture portions, in which a set of the cell capture portion, the flow channel, and the nucleic acid capture portion are arranged in a vertical direction, and a plurality of sets thereof are two-dimensionally arranged.

CITATION LIST

Patent Literature

SUMMARY OF INVENTION

Technical Problem

In order to carry out simultaneous DNA sequence analysis or gene expression analysis of many cells at a single-cell level at a low cost, it is effective to use a device which includes a porous membrane or two-dimensionally arranged beads as disclosed in Patent Literature 1. Upon using the device disclosed in Patent Literature 1, negative pressure is generated by aspiration via the bottom of the device. A cell suspension containing cells is introduced into the upper portion of the device such that the cell suspension flows in the top-to-bottom direction of the device. This flow causes each cell to be captured by the cell capture portion. The cell capture portion is designed such that it has a diameter (about several micrometers) smaller than the diameter of each cell (about 10 µm). Therefore, when a cell is captured, the flow of the cell suspension is blocked because the cell functions as a plug for the cell capture portion, thereby preventing the cell capture portion from further capturing a different cell. Next, a liquid for cell membrane lysis is introduced into a device upper portion so that a cell membrane is lysed, thereby causing an intracellular biomolecule to be eluted. Since the cell lysis solution flows in the top-to-bottom direction of the device, a biomolecule eluted in the nucleic acid capture portion provided in the lower portion of the cell capture portion such that the biomolecule is captured by the nucleic acid capture portion.

In order to efficiently capture an intracellular biomolecule, it is necessary to increase the surface area of a nucleic acid capture portion for capturing a biomolecule. More specifically, it is necessary to set the diameters of average holes that constitute a porous membrane serving as a nucleic acid capture portion to several micrometers or less. In addition, it may be desirable to set the membrane thickness of the porous membrane to several tens of micrometers or more. However, the use of a porous membrane having the above conditions often results in a large increase in pressure loss when a cell suspension is allowed to pass through the porous membrane, which might cause a decrease in the flow velocity of the cell suspension or make it difficult to control such flow velocity. In a case in which the flow velocity is slowed, a relatively large number of cells are adsorbed by portions other than the cell capture portion due to the influence of gravity or diffusion. When a cell membrane is (lysed) to elute intracellular biomolecules, biomolecules of cells adsorbed by portions other than the cell capture portion flow into a plurality of nucleic acid capture portions, which causes reduction of analysis accuracy.

Also when the surrounding area of the cell capture portion is washed after cell capture, washing efficiency significantly declines due to the slowed flow velocity. This may cause reduction of analysis accuracy as described above.

Even in a case in which the flow of a cell suspension is excessively rapid, cells pass through the cell capture portion because of their soft texture, which might cause a plurality of cells to be introduced into a nucleic acid capture portion. Even in a case in which two or more cells are introduced into one cell capture portion, if it is possible to confirm the introduction of two or more cells based on a microscopic image or the like, it would be possible to prevent reduction of overall analysis accuracy by omitting data obtained from the cell capture portion. However, in a case where two or more cells are introduced into the nucleic acid capture portion, it is difficult to observe the cells. It is also possible to conduct real-time observation upon cell capture so as to calculate how many cells have been introduced into the cell capture portion. However, in a case in which the flow velocity of the cell suspension is rapid, calculation itself could be difficult.

Upon elution of intracellular biomolecules, a solution containing biomolecules flows into a nucleic acid capture portion provided below a cell capture portion. At such time, biomolecules might flow into a nucleic acid capture portion adjacent to the nucleic acid capture portion (crosstalk) due to the influence of diffusion or the like. As a result of crosstalk generation, it is necessary to conduct sequence analysis based on a composition that differs from the original nucleic acid composition, which might cause reduction of analysis accuracy.

In view of the above, an object of the present invention is to provide a means and a method for simultaneously analyzing biomolecules from a plurality of cells at a single-cell level by capturing cells exclusively by a cell capture portion area so as to reduce crosstalk generated upon cell membrane lysis while maintaining a condition in which biomolecules are captured efficiently for the purpose of further improvement.

Solution to Problem

In order to achieve the above object, the device and system according to the present invention have the following configurations. Specifically, the device for capturing a biomolecule in a single cell according to the present invention comprises: a two-dimensional array having a plurality of single cell capture holes formed on one surface of a substrate, and biomolecule capture areas inside of the substrate each comprising a biomolecule capture member for capturing a biomolecule extracted from individual cells which are respectively captured by the single cell capture holes; a flow channel for flowing a sample, which comprises a plurality of cells to be assayed, from a 1st direction in parallel with the one surface of the substrate; and a structure provided on the surface of the substrate so as to be opposed to the 1st direction on the downstream side of each of the single cell capture holes. In addition, the system for capturing a biomolecule in a single cell according to the present invention comprises: a two-dimensional array having a plurality of single cell capture holes formed on one surface of a substrate, and biomolecule capture areas inside of the substrate each comprising a biomolecule capture member for capturing a biomolecule extracted from individual cells which are respectively captured by the single cell capture holes; a flow channel for flowing a sample, which comprises a plurality of cells to be assayed, from a 1st direction in parallel with the one surface of the substrate; a structure provided on the surface of the substrate so as to be opposed to the 1st direction on the downstream side of each of the single cell capture holes; a 1st application means which applies a 1st flow, and a 1st control means; and a 2nd application means which applies a 2nd flow that is orthogonal to the one surface of the substrate toward each biomolecule capture area from each corresponding single cell capture hole, and a 2nd control means, wherein the 1st and 2nd control means control the flow rate such that the flow rate of the 1st flow is greater than that of the 2nd flow upon cell capture and the flow rate of the 2nd flow is greater than that of the 1st flow upon biomolecule capture.

In addition, the method for capturing a biomolecule in each single cell from a sample comprising a plurality of cells according to the present invention comprises: providing the device or the system according to the present invention; flowing a sample, which comprises a plurality of cells to be assayed, via the flow channel of the device or system so as to generate a flow in parallel with one surface of a substrate of a two-dimensional array, thereby capturing individual cells by each of single cell capture holes on the two-dimensional array; generating a flow in parallel with the one surface of the substrate, thereby washing the two-dimensional array; and generating a flow that is orthogonal to the one surface of the substrate so as to lyse each captured cell, thereby capturing a biomolecule by a biomolecule capture member of the two-dimensional array.

Advantageous Effects of Invention

According to the present invention, it is possible to simultaneously analyze biomolecules from a plurality of cells at a single-cell level by capturing cells exclusively by a cell capture portion area so as to reduce crosstalk generated upon cell membrane lysis while maintaining a condition that biomolecules are efficiently captured. As a result, according to the device, system, and method of the present invention, it is possible to efficiently and securely capture a biomolecule in a single cell, thereby analyzing a single-cell biomolecule with high accuracy. Therefore, the device, system, and method are useful in the fields of gene expression analysis, cell function analysis, biological tissue analysis, diagnosis of disease, drug discovery, and the like.

BRIEF DESCRIPTION OF DRAWINGS

FIG. 10($b$) is a front view of a cell capture structure.

DESCRIPTION OF EMBODIMENTS

Figure 1:
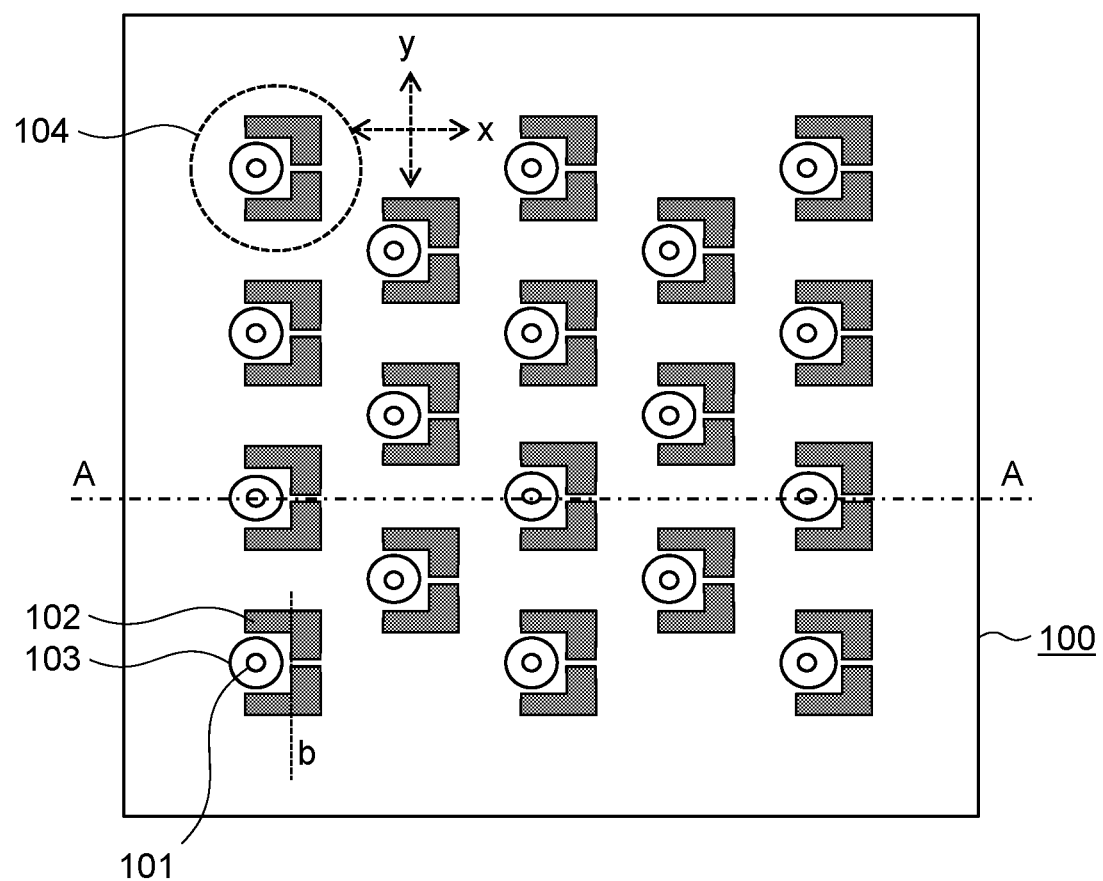
FIG. 1 is a plan view of a chip for capturing nucleic acid in a single cell.

The present invention provides a device, a system, and a method for capturing biomolecules in a single cell from a sample containing a plurality of cells with high efficiency and high accuracy by preparing a library (e.g., cDNA library) of biomolecules (e.g., mRNAs) from a biological tissue at a single-cell level resolution and conducting hybridization using a next-generation DNA sequencer or probes specific to genes to be analyzed for the final purpose of analyzing the expression of the biomolecules at a single-cell level resolution.

The term "biomolecule in a single cell or single-cell biomolecule" used in the present invention refers to a biomolecule contained in a single cell, which is a biomolecule from each single cell in a sample containing a plurality of cells. Similarly, the term "single-cell level resolution" refers to ability to analyze each single cell, which is specifically a biomolecule in a single cell, in a sample containing a plurality of cells.

The expression "capturing a biomolecule" used in the present invention means that a molecule contained in a cell is extracted so as to be separated from other cell components. Preferably, it refers to immobilization of such molecule. In addition, the term "gene expression analysis" refers to analysis of a biomolecule related to gene expression. Specifically, it refers to quantitative determination of the expression of a gene or biomolecule in a sample (e.g., a cell or a tissue section), for example, a target nucleic acid to be assayed, analysis of distribution of the expression of a gene (nucleic acid to be assayed) or biomolecule in a sample, or acquisition of data of a correlation between a specific position and the expression level of a gene (nucleic acid to be assayed) or biomolecule in a sample.

According to the present invention, a biomolecule to be captured or analyzed is not particularly limited as long as it is a biomolecule contained in a cell. Examples thereof include, nucleic acids (e.g., messenger RNA (mRNA), non-coding RNA (ncRNA), microRNA, genomic DNA, and fragments thereof), proteins (e.g., enzymes and antibodies), and low-molecular-weight compounds.

In one embodiment, a device for capturing each of a plurality of cells contained in a sample, extracting a biomolecule from each captured cell, and capturing the biomolecule (referred to as a "device for capturing biomolecule in a single cell") according to the present invention comprises:

a two-dimensional array having a plurality of single cell capture holes formed on one surface of a substrate, and biomolecule capture areas inside of the substrate each comprising a biomolecule capture member for capturing a biomolecule extracted from individual cells which are respectively captured by the single cell capture holes;

a flow channel for flowing a sample, which contains a plurality of cells to be assayed, from a 1st direction in parallel with the one surface of the substrate; and a structure provided on the surface of the substrate so as to be opposed to the 1st direction on the downstream side of each of the single cell capture holes.

A two-dimensional array is formed on a substrate, a plurality of single cell capture holes are formed on one surface of the substrate, and biomolecule capture areas are formed inside of the substrate. Such two-dimensional array is known in the art, for example, as described in Patent Literature 1.

For example, the substrate is not limited as long as it is made of a material commonly used in the art. Examples of such material include metals such as gold, silver, copper, aluminum, tungsten, molybdenum, chromium, platinum, titanium, and nickel; alloys such as stainless-steel, Hastelloy, Inconel, Monel, and duralumin; silicone; glass materials such as glass, silica glass, fused silica, synthetic silica, alumina, sapphire, ceramic, forsterite, and photosensitive glass; plastics such as a polyester resin, polystyrene, a polyethylene resin, a polypropylene resin, an acrylonitrile butadiene styrene (ABS) resin, dimethylpolysiloxane (PDMS), cyclic polyolefin, nylon, an acrylic resin, a fluorine resin, a polycarbonate resin, a polyurethane resin, a methylpentene resin, a phenol resin, a melamine resin, an epoxy resin, and a vinyl chloride resin; agarose, dextran, cellulose, polyvinyl alcohol, nitrocellulose, chitin, and chitosan. The material used for the substrate may preferably be a hydrophobic material so that adsorption of cells, a reagent, or the like can be reduced.

A technique for forming single cell capture holes on one surface of the substrate and biomolecule capture areas each having a biomolecule capture member inside of the substrate is also known in the art. In order to improve efficiency of biomolecule capture, it may be preferable to use a material having a large surface area for the biomolecule capture areas each having the biomolecule capture member. For example, it may be preferable to adopt a structure, which is filled with many beads, a porous structure, a mesh structure, or the like. In a case in which a bead is used as the biomolecule capture member, it is possible to prepare a bead from a resin material (e.g., polystyrene), an oxide (e.g., glass), a metal (e.g., iron), sepharose, or a combination thereof. In view of operational convenience, it may be preferable to use a magnetic bead. The size of the single cell capture hole needs to be smaller than the size of a cell to be captured but large enough to induce generation of a flow orthogonal to one surface of the substrate as described below. For example, the size can be 5 to 10 μm and preferably 8 to 10 μm, which should be appropriately changed depending on the type of cells to be captured. It is also possible to appropriately change positions of the single cell capture holes on the substrate and an interval therebetween depending on the type of cells to be captured. In order to ensure and promote the capture of a single cell in each hole, it may be preferable for the single cell capture holes to be alternately arranged (e.g., FIGS. 1 and 5).

A biomolecule capture member may have an appropriate probe depending on the type of a biomolecule to be captured, which is preferably a probe that specifically binds to the biomolecule. For example, in a case in which the biomolecule is mRNA, a DNA probe having a poly-T sequence can be used. A DNA probe having a poly-T sequence, i.e., oligo (dT), can be synthesized by an ordinary method. The degree of polymerization of oligo (dT) may be at a degree of polymerization at which oligo (dT) can be hybridized with the poly-A sequence of mRNA, thereby allowing mRNA to be captured by a biomolecule capture member to which oligo (dT) is immobilized. For example, the degree of polymerization can be about 10 to 30 bases, 10 to 20 bases, or 10 to 15 bases. In a case in which the biomolecule is noncoding RNA (ncRNA), microRNA, or genomic DNA, it is possible to use a DNA probe comprising a random sequence or a DNA probe having a sequence complementary to a specific target sequence. In addition, in a case in which the biomolecule is a protein or a low-molecular-weight compound, it is possible to use a 1st binding molecule (e.g., an antibody or aptamer) that specifically binds to the biomolecule, and a 1st DNA probe bound to the 1st binding molecule. Then, a 2nd binding molecule (preferably a molecule of the same type of the above-described binding molecule, for example, an antibody or aptamer) that binds to the above-described biomolecule so as to sandwich the biomolecule with the 1st binding molecule, and a 2nd DNA probe bound to the 2nd binding molecule are added. When a target biomolecule is present, the above-described DNA probe is ligated to the 2nd DNA probe, thereby forming a ring probe specific to the biomolecule. This method is called a "proximity ligation method" (e.g., Malin Jarvius et al. Molecular & Cellular Proteomics 6 (9) p. 1500, 2007), which is useful for construction of a DNA library for proteins.

The probe can be immobilized to the biomolecule capture member by any method known in the art. For example, the probe can be immobilized to a surface of a bead or a surface or inside of a porous membrane by covalent bond, ion bond, physical adsorption, or biological binding (e.g., binding between biotin and avidin or streptavidin, or binding between an antigen and an antibody). It is also possible to immobilize the probe via a spacer sequence to the biomolecule capture member. In a case in which a protein or a low-molecular-weight compound is treated as a biomolecule by the proximity ligation described above, it is also possible to immobilize the 1st binding molecule to the biomolecule capture member.

The two-dimensional array or the substrate may preferably be treated by surface coating to prevent adsorption of other substances (e.g., nucleic acids and proteins).

A flow channel is also known in the art. It may be integrated with the substrate or the two-dimensional array or it may be prepared separately therefrom and then connected thereto. A sample to be assayed, which contains a plurality of cells, can be flowed through this flow channel in a 1st direction in parallel with one surface of the substrate.

A structure is formed on the substrate of the two-dimensional array. The structure is formed on the surface of the downstream side of the 1st direction of each of the single cell capture holes such that the structure is opposed to the 1st direction. The shape of the structure is not particularly limited as long as it is appropriate for cell capture. For example, the structure can be in the square U-shaped form (FIG. 1), the triangular cylinder form (FIG. 9(*a*)), the circular cylinder form (FIG. 9 (*b*)), or the concave form (FIG. 9(*c*), FIG. 10(*a*)). The size of the structure may be determined to ensure the capture of a single cell alone such that the height and width thereof are 20 µm or less, preferably 10 to 18 µm, and more preferably 10 to 15 µm. It may be preferable that a slit or a hole is formed especially on the downstream side of a 1st flow such that a sample liquid excluding cells can be readily discharged. The structure may be integrated with the two-dimensional array or they may be separately prepared and then bound to each other.

The device having the above-described configuration according to the present invention comprises such structure. Therefore, it is possible to exclusively capture individual cells by each of the single cell capture holes from a sample containing a plurality of cells. It is also physically possible to reduce the influence of introduction of a biomolecule (e.g., mRNA) eluted from a captured cell into a different site due to the influence of diffusion or the like, and in particular, the influence of introduction of such biomolecule into a different biomolecule capture area.

In another embodiment, the system for capturing a biomolecule in a single cell according to the present invention comprises:

a two-dimensional array having a plurality of single cell capture holes formed on one surface of a substrate, and biomolecule capture areas inside of the substrate each comprising a biomolecule capture member for capturing a biomolecule extracted from individual cells which are respectively captured by the single cell capture holes;

a flow channel for flowing a sample, which comprises a plurality of cells to be assayed, from a 1st direction in parallel with the one surface of the substrate;

a structure provided on the surface of the substrate so as to be opposed to the 1st direction on the downstream side of each of the single cell capture holes;

a 1st application means which applies a 1st flow, and a 1st control means; and a 2nd application means which applies a 2nd flow that is orthogonal to the one surface of the substrate toward each biomolecule capture area from each corresponding single cell capture hole, and a 2nd control means, wherein the 1st and 2nd control means control the flow rate such that the flow rate of the 1st flow is greater than that of the 2nd flow upon cell capture and the flow rate of the 2nd flow is greater than that of the 1st flow upon biomolecule capture.

The application means which applies a flow is known in the art. For example, a syringe, a pump, an aspiration apparatus, a pressurization apparatus, or the like can be used. The control means is also not particularly limited as long as it is a means for determining/controlling the flow rate. According to the present invention, it is possible to secure the capture of a cell in each single cell capture hole upon cell capture by controlling the flow rate of a 1st flow (parallel flow) applied by the 1st application means and the flow rate of a 2nd flow (orthogonal flow) by the 2nd application means using the 1st control means and the 2nd control means. Thus, it is possible to wash the substrate or two-dimensional array which retains a cell captured by each single cell capture hole and/or efficiently capture a biomolecule in a biomolecule capture area without generation of crosstalk. Specifically, upon cell capture and washing of the two-dimensional array, the flow rate of a parallel flow is controlled to be greater than the flow rate of an orthogonal flow. Upon biomolecule capture, the flow rate of an orthogonal flow is controlled to be greater than the flow rate of a parallel flow.

In addition, the system for capturing a biomolecule in a single cell according to the present invention may further comprises a means for returning the plurality of cells discharged on the downstream side of the 1st direction via the 1st flow back to the flow channel for flowing a sample containing the plurality of cells. For example, a tube or a pipe that connects an outlet formed on the substrate or the two-dimensional array with the above-described flow channel can be used.

The system for capturing a biomolecule in a single cell according to the present invention may further comprise a reagent introduction means, a temperature control means, an optical observation means, a moving stage, and the like.

The system having the above-described configuration according to the present invention comprises the above-described structure. Therefore, it is possible to exclusively capture individual cells by each of the single cell capture holes from a sample containing a plurality of cells. It is also physically possible to reduce the influence of introduction of a biomolecule (e.g., mRNA) eluted from a captured cell into a different site due to the influence of diffusion or the like, and in particular, the influence of introduction of such biomolecule into a different biomolecule capture area. In addition, as a means for applying a flow onto the substrate and a means for controlling the flow rate upon cell capture and biomolecule capture are provided, it is possible to efficiently wash cells adsorbed by the substrate other than cells captured by the structure so as to capture a biomolecule (e.g., mRNA) eluted from a captured cell in a biomolecule capture area with high capture efficiency and reduced crosstalk.

In another embodiment, the method for capturing a biomolecule in each single cell from a sample containing a plurality of cells (herein also referred to as a "method for capturing biomolecule in a single cell") comprises:

providing the device or the system according to the present invention;

flowing a sample, which comprises a plurality of cells to be assayed, via the flow channel of the device or system so as to generate a flow in parallel with one surface of a substrate of a two-dimensional array, thereby capturing individual cells by each of single cell capture holes on the two-dimensional array;

generating a flow in parallel with the one surface of the substrate, thereby washing the two-dimensional array; and generating a flow that is orthogonal to the one surface of the substrate so as to lyse each captured cell, thereby capturing a biomolecule by a biomolecule capture member of the two-dimensional array.

The sample is not particularly limited as long as it is a biologically derived sample containing a plurality of cells. An organism that is the origin of a sample is also not particularly limited. A sample from any organisms such as a vertebrate (e.g. a mammal, bird, reptile, fish, or amphibian), an invertebrate (e.g. an insect, nematode, or crustacean), a protozoa, a plant, a fungus, a bacterium, or a virus can be used. It is necessary for a sample to be in the form that is flowable in the flow channel when used in the device, system or method according to the present invention. Therefore, in a case in which a sample is a solid sample (e.g., a tissue section), it may be preferable to lyse or suspend a solid sample in a solvent to form a liquid sample. In addition, in a case in which a sample is a gaseous sample (e.g., air or exhaled air), it may be preferable to suspend cells contained in a gaseous sample in a solvent to form a liquid sample. A sample preparation method is conventionally carried out in the art. A person skilled in the art can readily understand such method.

A sample, which contains a plurality of cells to be assayed, is flowed via the flow channel of the device or system so as to generate a flow in parallel with one surface of a substrate of a two-dimensional array, thereby capturing individual cells by each of the single cell capture holes on the two-dimensional array. Since a structure is formed on the two-dimensional array, each of the plurality of cells contained in the sample can be captured by the single cell capture hole.

Next, an appropriate solvent, buffer, or the like is allowed to flow so as to generate a flow in parallel with one surface of the substrate, thereby washing the surface of the two-dimensional array. It is possible to wash unnecessary cells and components adsorbed by the substrate while allowing cells being captured by the single cell capture holes on the substrate.

Then, a flow that is orthogonal to the one surface of the substrate is generated so as to lyse each captured cell, thereby capturing a biomolecule by the biomolecule capture member of the two-dimensional array. For example, it is possible to lyse cells using a cell lysis reagent known in the art so as to extract nucleic acids contained in the cells. Cells may be lysed using, for example, a proteolytic enzyme such as proteinase K, a chaotropic salt such as guanidine thiocyanate-guanidine hydrochloride, a surfactant such as Tween or SDS, or a commercially available cell lysis reagent, thereby making it possible to elute nucleic acids contained in the cells, i.e., DNA and RNA. In a case in which mRNA is captured as a biomolecule, it is possible to degrade DNA by a DNA degrading enzyme (DNase) and then capturing RNA alone.

According to the method for capturing biomolecule in a single cell, it is possible to capture individual cells by each of the single cell capture holes from a sample containing a plurality of cells so as to securely capture a single-cell-derived biomolecule from each captured cell with high efficiency by using the device or system of the present invention.

Specific embodiments of the present invention are hereinafter described with reference to the drawings.

Example 1

In this Example, a device and a system having the configuration of the present invention used for capturing a nucleic acid as a single-cell biomolecule from a sample comprising a plurality of cells are described.

Figure 2:
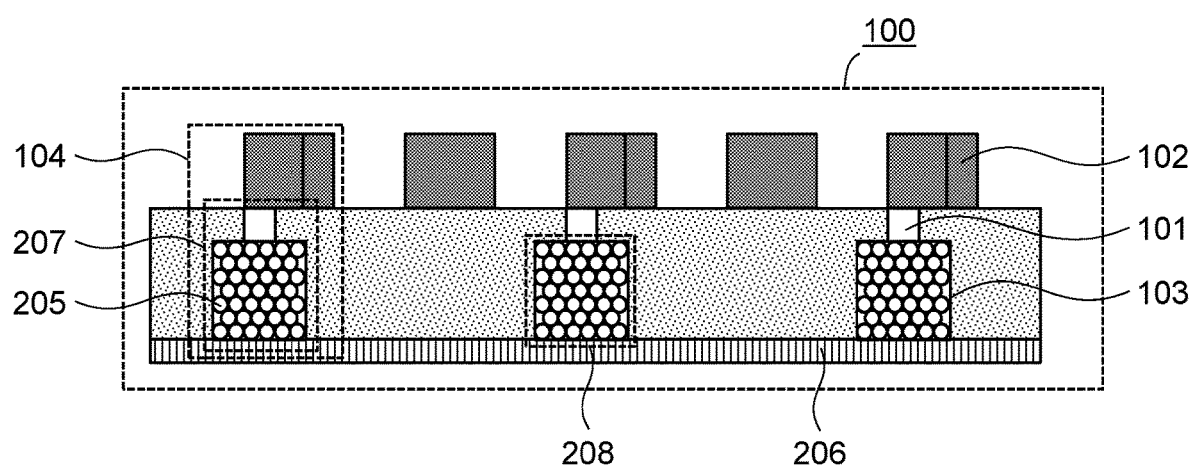
FIG. 2 is a cross-sectional view of a chip for capturing nucleic acid in a single cell.

FIG. 1 is a plan view of a chip 100 for capturing nucleic acid in a single cell. FIG. 2 is an A-A cross-sectional view of the chip for capturing nucleic acid in a single cell of FIG. 1. As the chip 100 for capturing nucleic acid in a single cell, a chip having a substrate made of dimethylpolysiloxane (PDMS) prepared by injection molding and laser processing was used. The chip had a configuration in which single-cell nucleic acid capture areas 104 were arranged alternately in the two-dimensional array form, the single-cell nucleic acid capture areas 104 each having a reactor 207, in which a cell capture hole 101 and a nucleic acid capture hole 103 were arranged in that order vertically, and a cell capture structure 102, which was provided in the vicinity of the cell capture hole 101. The single-cell nucleic acid capture areas 104 were arranged in a row alternately one below the other in the x axis direction at 200-μm intervals in the x and y directions. In one chip 100 for capturing nucleic acid in a single cell, the single-cell nucleic acid capture areas 104 (18 areas in total) are provided. When a cell is captured, a cell suspension (sample) flows in the left-to-right direction along the x axis direction in FIG. 1.

As illustrated in FIG. 2, the cell capture hole 101 and the nucleic acid capture hole 103 are formed on the upper and lower portions of a single reactor, respectively. A cell capture structure 102 is in the square U-shaped form, and is provided along the downstream direction of the flow of a cell suspension in the vicinity of the cell capture hole 101. A slit is formed along the downstream direction of the flow of a cell suspension in the cell capture structure 102. In order to prevent a captured cell from flowing out from the structure, the slit width was set to 5 μm, which is smaller than the cell size. The height of the cell capture structure 102 needs to be smaller than the height of two cells such that a plurality of cells are not captured by an identical single cell structure. The size of each cell is approximately 10 μm. Therefore, the height of the cell capture structure may preferably be 20 μm or less. In this Example, the height of the cell capture structure 102 was set to 15 μm. In addition, a cavity depth of the cell capture structure 102 in the square U-shaped form, which was formed in the x axis direction, was set to 10 μm, which was smaller than the height of a single cell. Further, in order to allow mRNA, which is a biomolecule of a captured cell, to efficiently flow into the nucleic acid capture hole 103, it may be desirable to dispose the cell capture structure 102 such that the cell capture hole 101 is positioned immediately below the captured cell. In this Example, the cell capture structure 102 was disposed such that a distance between a face of the cell capture structure 102, which is along line b in FIG. 1, and the center of the cell capture hole 101 was adjusted to 10 μm. The width of the cell capture structure in the y axis direction needs to be less than the height of two cells such that a plurality of cells are not captured by an identical single cell structure, which means 20 μm or less. In this Example, the width was set to 18 μm.

The nucleic acid capture hole 103 is filled with magnetic beads 205 each having a diameter of 1 μm, thereby defining a nucleic acid capture area 208. The opening diameter of the cell capture hole 101 was set to 5 μm, and the opening diameter of the nucleic acid capture hole 103 was set to 70 μm. A porous sheet 206 made of alumina, which had an opening about 500 nm in size was disposed so as to prevent magnetic beads 205 from leaking out toward the lower part in FIG. 2. A PDMS-made substrate was bonded to the porous sheet 206 via plasma bonding. Instead of a PDMS-made substrate, a resin chip obtained by injection molding of a different resin (e.g., polycarbonate, cyclic polyolefin, or polypropylene) may be used. Alternatively, a resin chip made by nanoimprint technology or semiconductor processing can be used.

In this Example, a sheet, on which magnetic beads each modified with a DNA probe for capturing mRNA were arranged to form a two-dimensional array, was used as a device for capturing nucleic acid in a single cell. However, a known porous membrane such as one described in Patent Literature 1 may be used. Although magnetic beads were used in this Example, it is also possible to prepare beads from a resin material (e.g., polystyrene), an oxide (e.g., glass), a metal (e.g., iron), sepharose, or a combination thereof, instead of magnetic beads.

Figure 3:
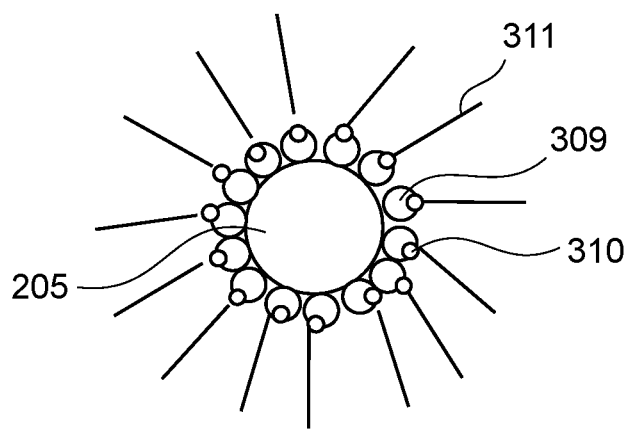
FIG. 3 is a schematic view of a magnetic bead.

FIG. 3 is a schematic view of a magnetic bead 205 for capturing nucleic acid. The surface of the magnetic bead 205 is modified with many streptavidin molecules 309. A DNA probe 311 for capturing mRNA, which has a 5' end bound to biotin 310, is bound to via each streptavidin molecule 309 to the magnetic bead 205.

Figure 4:
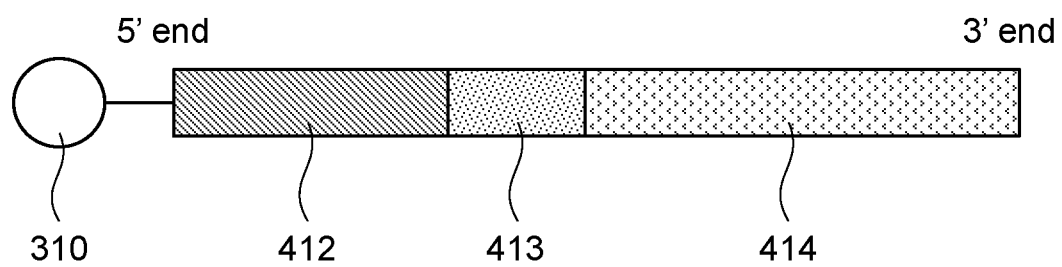
FIG. 4 is a schematic view of a DNA probe for capturing mRNA.

FIG. 4 is a schematic view of one example of the DNA probe 311 for capturing mRNA. The DNA probe 311 for capturing mRNA, which is a DNA probe having a 5' end bound to biotin 310, comprises, from 5' end, a PCR amplification consensus sequence (Forward) 412, a cell recognition tag sequence 413, and a nucleic acid capture sequence 414. Oligo (dT) was used herein as the nucleic acid capture sequence. Oligo (dT) used herein may be hybridized with the poly-A sequence of mRNA, thereby allowing capture of mRNA in a sample cell. The degree of polymerization of oligo (dT) may be at a degree of polymerization at which oligo (dT) can be hybridized with the poly-A sequence of mRNA, thereby allowing a magnetic bead 205, to which a nucleic acid probe containing oligo (dT) is immobilized, to capture mRNA. For example, the degree of polymerization may be about 10 to 30 bases, 10 to 20 bases, or 10 to 15 bases. In addition, although a nucleic acid to be captured was mRNA in this Example, a random sequence or a sequence complementary to a portion of a target nucleic acid to be assayed may be used as the nucleic acid capture sequence in a case in which, for example, a nucleic acid to be captured is microRNA or genomic DNA. By introducing the PCR amplification consensus sequence 412 into the DNA probe 311 for capturing mRNA, the resulting sequence can be used as a common primer in the subsequent PCR amplification step. In addition, by introducing the cell recognition tag sequence 413 (e.g., 5 base) into the DNA probe 311 for capturing mRNA, $4^5$ (=1024) positions or areas (e.g., $4^5$=1024 single cells) can be recognized, thereby making it possible to identify a cell (or position or area) as the origin from which the final sequence data of a next-generation sequencer are obtained. Such tag sequence is described in detail in, for example, WO2014/141386.

Figure 5:
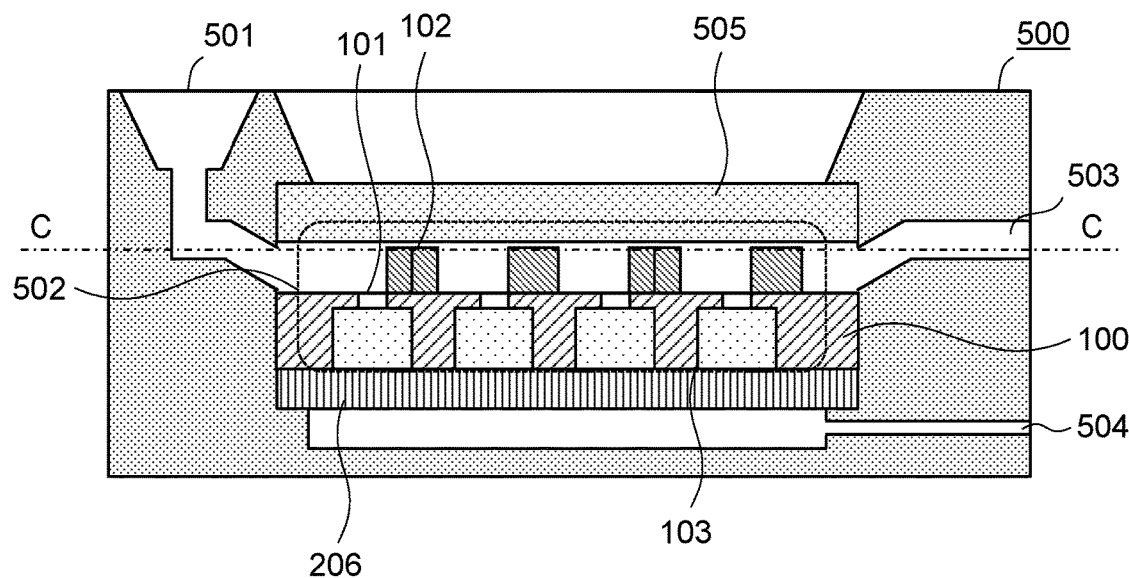
FIGS. 5($a$)-($b$) is a schematic view of a device for capturing nucleic acid in a single cell.
Figure 5:
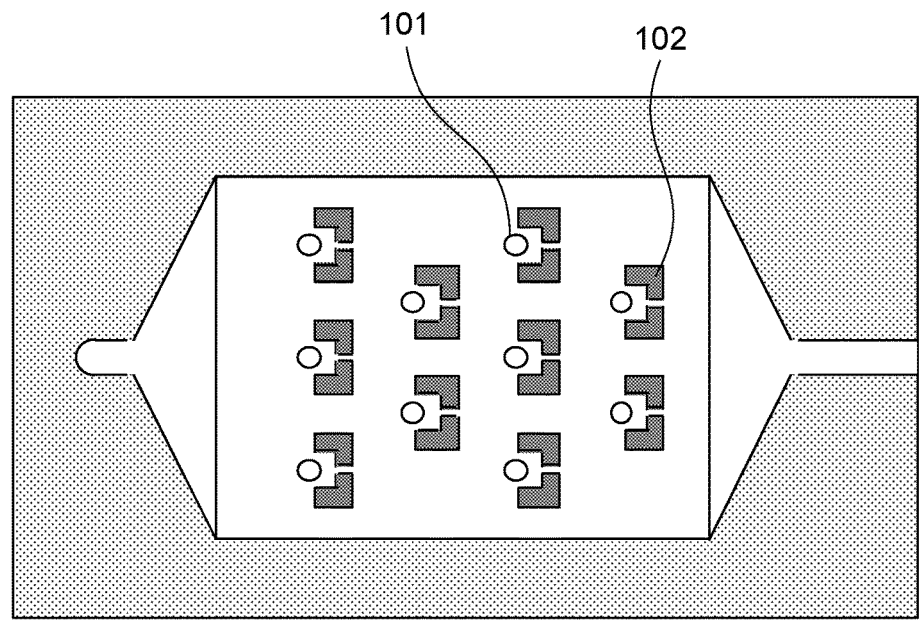

FIG. 5 (a) is a cross-sectional view orthogonal to a face of the chip 100 for capturing nucleic acid in a single cell of the device 500 for capturing nucleic acid in a single cell to which the present invention is applied. In addition, FIG. 5 (b) is a cross-sectional view in parallel with one face of the chip 100 for capturing nucleic acid in a single cell, which corresponds to a C-C cross-section in FIG. 5 (a). The device 500 for capturing nucleic acid in a single cell comprises: an inlet 501 for introducing a cell suspension (sample), a reagent, and a washing buffer; a reaction field 502 where the chip 100 for capturing nucleic acid in a single cell is provided for capturing cells and capturing nucleic acids; and a 1st outlet 503 and a 2nd outlet 504 for discharging a solution.

In this Example, although an acrylic resin was used as a material for the device 500 for capturing nucleic acid in a single cell, a different resin or metal may be used. In consideration of the ease of cell observation upon cell capture, it may be preferable to use an optically transparent material. In addition, it is necessary to avoid using, as a material that constitutes a flow channel, a material that may inhibit nucleic acid capture or cDNA synthesis reaction. For example, it may be preferable to avoid using aluminum or the like because it may inhibit cDNA synthesis reaction. A window 505 formed with an optically transparent material was disposed immediately above the reaction field 502 of the device 500 for capturing nucleic acid in a single cell in order to optically observe the chip 100 for capturing nucleic acid in a single cell. In this Example, a glass plate made of quartz (silica) was used. In a case in which a material for the device for capturing nucleic acid in a single cell is optically transparent, it is not necessary to select a different material as a material used immediately above the reaction field 502. In addition, in a case in which it is not necessary to optically observe the chip 100 for capturing nucleic acid in a single cell, even when a material for the device for capturing nucleic acid in a single cell is not an optically transparent material, it is not necessary to select a different material as a material used immediately above the reaction field 502. It is necessary to set a distance between an objective lens and the surface of the chip 100 for capturing nucleic acid in a single cell to not more than a working distance of an objective lens. It is also necessary to set a thickness of the device 500 for capturing nucleic acid in a single cell disposed immediately above the reaction field, including the height of the flow channel, to not more than a working distance of an objective lens.

Figure 6:
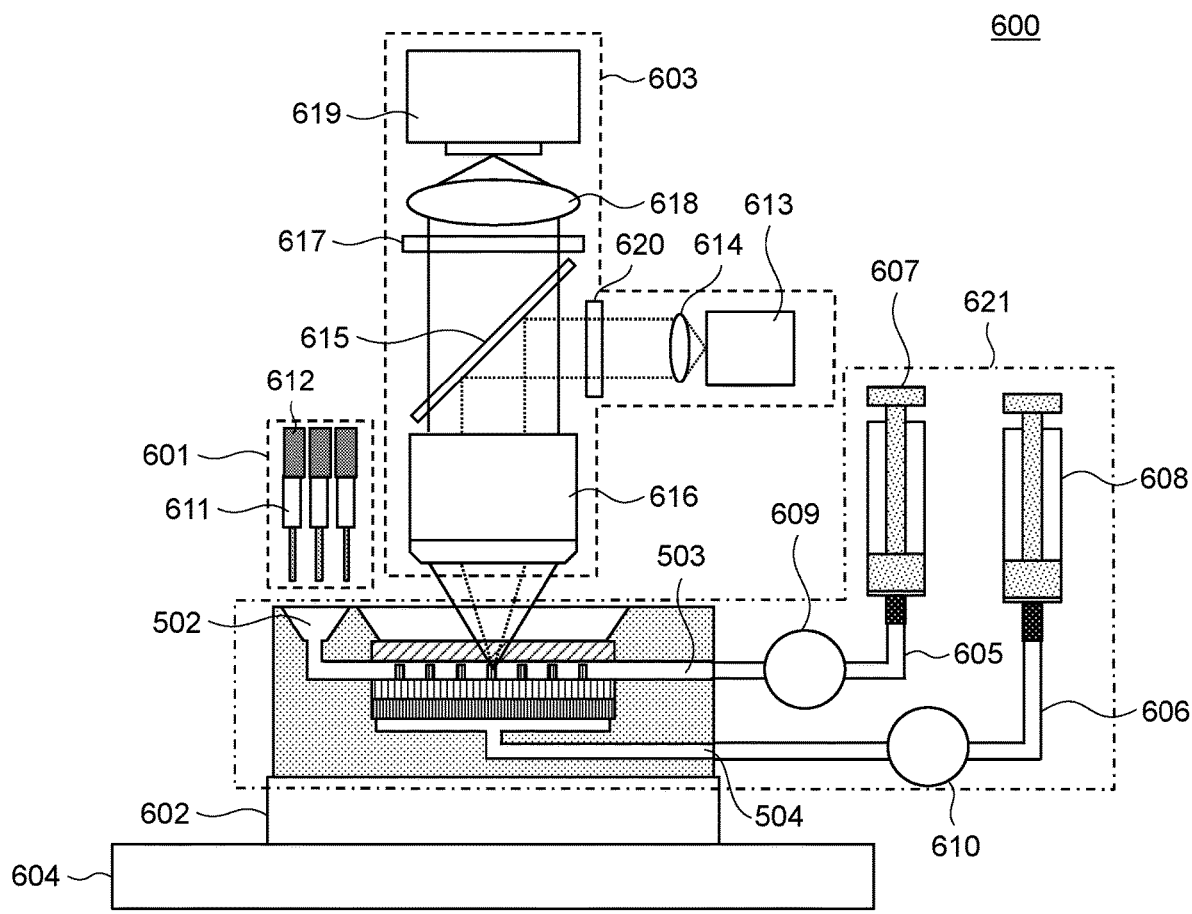
FIG. 6 is a schematic view of a system for capturing nucleic acid in a single cell.

FIG. 6 is a schematic view of a system 600 for capturing nucleic acid in a single cell. The system 600 for capturing nucleic acid in a single cell is configured to comprise, in addition to the device for capturing nucleic acid in a single cell: a liquid feeding unit 621; a reagent dispensing unit 601; a temperature control unit 602 for controlling the temperature of the device for capturing nucleic acid in a single cell; an optical observation unit 603 for optically observing the chip 100 for capturing nucleic acid in a single cell; and a moving stage unit 604 for allowing the device 500 for capturing nucleic acid in a single cell to move to a desired position.

The liquid feeding unit 621 is configured as described below. A 1st syringe 607 and a 2nd syringe 608 are connected via a 1st discharging tube 605 and a 2nd discharging tube 606 to a 1st outlet 503 and a 2nd outlet 504 of the device for capturing nucleic acid in a single cell, respectively. The discharging tubes are provided with 1st and 2nd mass flow controllers 609 and 610 capable of measuring and controlling the follow volume of the corresponding discharging tube. The 1st syringe 607 can generate a flow (parallel flow) in parallel with a face of the chip 100 for capturing nucleic acid in a single cell, and the 2nd syringe 608 can generate a flow orthogonal to the face (orthogonal flow).

The reagent dispensing unit 601 is provided with a reagent-accommodating dispenser 611 for accommodating and dispensing a reagent or a sample and a dispensing pressurizer 612 for pressurizing the reagent-accommodating dispenser 611 for dispensing a reagent or a sample for a certain period of time. The reagent-accommodating dispenser is configured to have a capillary formed with a polypropylene resin and glass. The reagent-accommodating dispenser dispenses a sample or reagent from the tip of the capillary when pressurized by the upper portion of the accommodation section made of a polypropylene resin, which accommodates the sample or reagent, at a certain level of pressure for a certain period of time. It is possible to pressurize each reagent-accommodating dispenser 611 independently. In this Example, the temperature of the reagent-accommodating dispenser 611 was not controlled. However, it is possible to control the temperature so as to prevent deterioration of a reagent (at an especially low temperature (e.g., 4° C.)).

The temperature control unit 602 is configured to have a combination of a Peltier element and a heater, thereby making it possible to control the temperature inside of the device 500 for capturing nucleic acid in a single cell between 4° C. and 85° C. More specifically, a highly thermally conductive metal (e.g., copper) is adhered to a surface of a Peltier element with an adhesive, and a heater is installed inside the metal. The metal is connected via a thermally conductive sheet to the device 500 for capturing nucleic acid in a single cell.

The optical observation unit 603 is configured to have a light source 613 comprising a halogen lamp for exiting GFP (Ex/Em=483/506 nm) used as a phosphor for labeling a cell as a sample; a condenser lens 614; an optical filter 620; a dichroic mirror 615; an objective lens 616; an optical filter 617; an imaging lens 618; and a CCD camera 619 described below. Light from the light source 613 is converted into a parallel luminous flux by the condenser lens 614. A wavelength around 480 nm is excluded by the optical filter 620, which is a band-path filter with a center wavelength of 480 nm. The light is reflected by the dichroic mirror 615 that reflects light with a wavelength of 500 nm or less. The reflected light is condensed by the objective lens 616, thereby irradiating a cell captured by the chip 100 for capturing nucleic acid in a single cell in the device 500 for capturing nucleic acid in a single cell with the light. Fluorescence emitted from the irradiated cell is collected by the objective lens 616 and permeates through the dichroic mirror 615. Thus, background light is removed by the optical filter 617 that cuts off light with a wavelength of 500 nm or less, and the CCD camera 619 forms an image using the imaging lens 618. In this Example, a configuration of an incident-light fluorescence microscope was employed. Alternatively, a configuration of an incident-light bright field or dark field microscope for directly observing cells may be employed. In addition, in a case in which the chip 100 for capturing nucleic acid in a single cell is formed with an optically transparent material, observation may be carried out by irradiation of excitation light or illuminating light from under the device 500 for capturing nucleic acid in a single cell or based on the configuration of a phase-difference microscope.

The moving stage unit 604 comprises an automatic moving stage. The temperature control unit 602 and the device 500 for capturing nucleic acid in a single cell are provided on the moving stage. The moving stage is connected to the temperature control unit 602 via a heat insulating material to the temperature controlled by the temperature control unit 602 does not influence the moving stage. The moving stage unit 604 allows the device 500 for capturing nucleic acid in a single cell to move to a position at which a reagent can be dispensed or a position for cell assay from the reagent dispenser 611.

Example 2

In this Example, a method for capturing a nucleic acid as a single-cell biomolecule from a sample comprising a plurality of cells and conducting gene expression analysis at a single-cell level resolution using a device or system having the configuration of the present invention is described.

Figure 7:
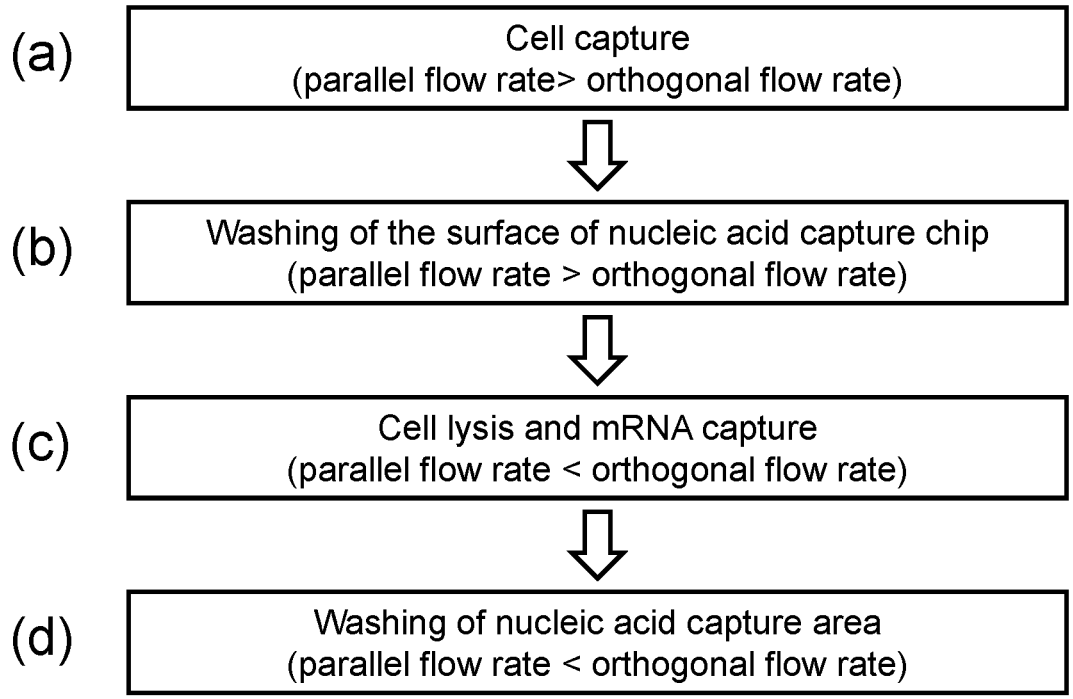
FIGS. 7($a$)-($d$) shows steps from a cell capture step to an mRNA capture step of a method for capturing nucleic acid in a single cell.

At first, steps from introducing a cell suspension as a sample to capturing intracellular mRNA are described below. As illustrated in FIG. 7, the main steps include cell capture in a chip 100 for capturing nucleic acid in a single cell (FIG. 7 (a)), washing of a surface of the chip 100 for capturing nucleic acid in a single cell (FIG. 7 (b)), cell lysis and mRNA capture (FIG. 7 (c)), and washing of a single-cell nucleic acid capture area 104 (FIG. 7 (d)).

More specifically, the following steps are carried out. A cell suspension was prepared by carefully washing about not more than 50 cells with 500 μL of 1×PBS so as not to damage the cells, removing PBS to a possible extent, and adding 20 μL of a 1×PBS buffer. GFP used as a phosphor has been incorporated into the cells in advance. The device 500 for capturing nucleic acid in a single cell is allowed to move by the moving stage unit 604 such that the inlet 501 is arranged under the reagent-accommodating dispenser 611 that is filled with a cell suspension. The reagent-accommodating dispenser 611 is pressurized by the dispensing pressurizer 612 at a certain pressure for a certain period of time, thereby introducing the cell suspension into the inlet 501. The 1st syringe 607 is pulled to generate a parallel flow, thereby allowing a nucleic acid capture structure 102 on the chip 100 for capturing nucleic acid in a single cell to capture cells (FIG. 7 (a)). At such time, it is possible to generate an orthogonal flow by pulling the 2nd syringe 608. Note that the flow rate of a parallel flow is adjusted to be greater than the flow rate of the orthogonal flow by the 1st and 2nd mass flow controllers 609 and 610. Next, the device 500 for capturing nucleic acid in a single cell is allowed to move by the moving stage unit 604 such that the inlet 501 is arranged under the reagent-accommodating dispenser 611 that is filled with a 1×PBS buffer serving as a washing buffer. The reagent-accommodating dispenser 611 is pressurized by the dispensing pressurizer 612 at a certain pressure for a certain period of time, thereby introducing the 1×PBS buffer into the inlet 501. The 1st syringe 607 is pulled to generate a parallel flow so as to wash the surface of the chip 100 for capturing nucleic acid in a single cell, thereby washing off adsorbed cells other than cells adsorbed by the cell capture structure (FIG. 7 (b)). At such time, it is possible to generate an orthogonal flow by pulling the 2nd syringe 608. Note that the flow rate of a parallel flow is adjusted to be greater than the flow rate of the orthogonal flow by the 1st and 2nd mass flow controllers 609 and 610. The device 500 for capturing nucleic acid in a single cell is allowed to move by the moving stage unit 604 such that the objective lens 616 is positioned immediately above the chip 100 for capturing nucleic acid in a single cell, thereby confirming a relationship between each cell capture hole 101 and the number of captured cells.

Next, the device 500 for capturing nucleic acid in a single cell is allowed to move by the moving stage unit 604 such that the inlet 501 is arranged under the reagent-accommodating dispenser 611 that is filled with a Lysis solution prepared with 39.5 µL of a RealTime ready Lysis buffer (Roche), 39.5 µL of Protector (Roche), and 0.5 µL of Protector RNase Inhibitor (Roche). The reagent-accommodating dispenser 611 is pressurized by the dispensing pressurizer 612 at a certain pressure for a certain period of time, thereby introducing the Lysis solution into the inlet 501. An orthogonal flow is generated by pulling the 2nd syringe 608. Cells are lysed with the Lysis solution such that intracellular mRNA is eluted. The orthogonal flow allows eluted mRNA to continuously flow from the cell capture hole 101 toward the nucleic acid capture hole 103. In the above process, mRNA is captured by an oligo (dT) portion of a DNA probe for capturing mRNA immobilized to a magnetic bead 205 (FIG. 7 (c)). At such time, it is possible to generate a parallel flow by pulling the 1st syringe 607. Note that the flow rate of an orthogonal flow is adjusted to be greater than the flow rate of the parallel flow by the 1st and 2nd mass flow controllers 609 and 610. According to the present invention, since the cell capture structure exists, it is physically possible to reduce the influence of diffusion or the like that causes mRNA eluted from a captured cell to be introduced into a site other than a cell capture hole, in which the cell is captured.

Next, the device 500 for capturing nucleic acid in a single cell is allowed to move by the moving stage unit 604 such that the inlet 501 is arranged under the reagent-accommodating dispenser 611 that is filled with a 1×PBS buffer serving as a washing buffer. The reagent-accommodating dispenser 611 is pressurized by the dispensing pressurizer 612 at a certain pressure for a certain period of time, thereby introducing the 1× PBS buffer into the inlet 501. The 2nd syringe 608 is pulled to generate an orthogonal flow so as to wash the nucleic acid capture area 208, thereby washing off excess mRNA, biological substances other than mRNA, and the Lysis solution (FIG. 7 (d)).

Figure 8:
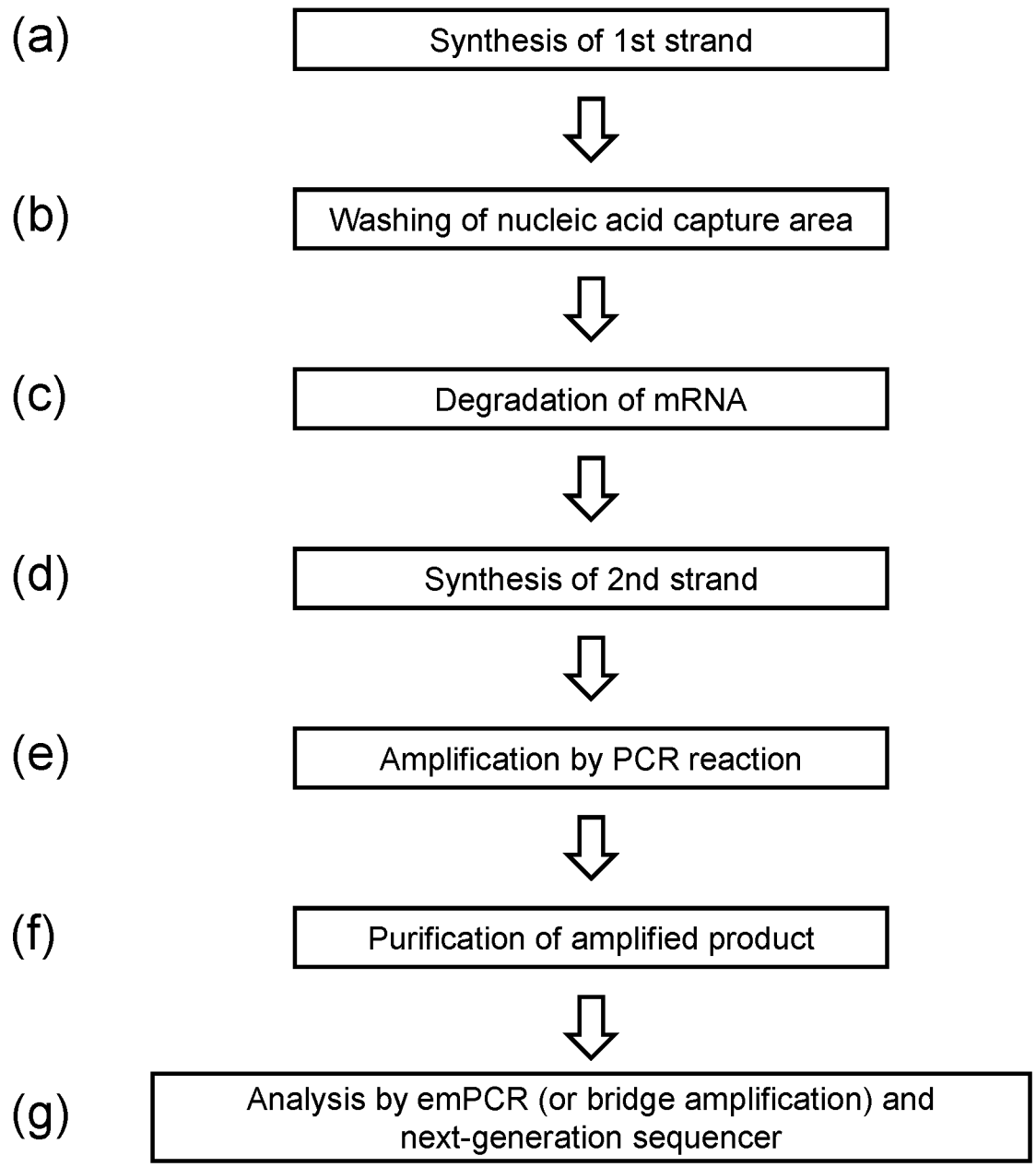
FIGS. 8($a$)-($g$) shows steps from a 1st strand synthesis step to a step of obtaining a gene expression profile after the implementation of a method for capturing nucleic acid in a single cell.

Next, the steps of obtaining a gene expression profile by a next-generation (large-scale) sequencer following the steps illustrated in FIG. 7 are described below. As illustrated in FIG. 8, the main steps include synthesis of a 1st strand (cDNA) (FIG. 8 (a)), washing of the nucleic acid capture area (FIG. 8 (b)), mRNA degradation (FIG. 8 (c)), synthesis of a 2nd strand (FIG. 8 (c)), amplification by a PCR reaction (FIG. 8 (d)), purification of an amplified product (FIG. 8 (e)), and analysis by emPCR and a next-generation DNA sequencer (FIG. 9 (f)).

More specifically, the following steps are conducted. The device 500 for capturing nucleic acid in a single cell is allowed to move by the moving stage unit 604 such that the inlet 501 is arranged under the reagent-accommodating dispenser 611 that is filled with a reverse transcription solution prepared by mixing 4 µL of a 5× First strand buffer (Invitrogen), 4 µL of 10 mM dNTP (Invitrogen), 4 µL of II (reverse transcriptase, Invitrogen), and 4 µL of RNaseOUT (Invitrogen). The reagent-accommodating dispenser 611 is pressurized by the dispensing pressurizer 612 at a certain pressure for a certain period of time, thereby introducing the reverse transcription solution into the inlet 501. The 2nd syringe 608 is pulled to generate an orthogonal flow, thereby allowing the solution to pass through each reactor 207 of the chip 100 for capturing nucleic acid in a single cell. A reverse transcription reaction was completed by terminating aspiration of a solution by the 2nd syringe 608 in a state in which the solution still remains on the chip 100 for capturing nucleic acid in a single cell, increasing the temperature inside of the device 500 for capturing nucleic acid in a single cell to 37° C. using the temperature control unit 602 so as to allow the solution to stand still for 10 minutes, increasing the temperature to 50° C., and maintaining the temperature for 45 minutes, thereby synthesizing a 1st strand DNA (cDNA) having a sequence complementary to mRNA (FIG. 8 (a)).

After synthesis of the cDNA strand, the temperature inside of the device 500 for capturing nucleic acid in a single cell was increased to 85° C. and the temperature was maintained for 90 seconds by the temperature control unit 602, thereby inactivating reverse transcriptase. After the inactivation of reverse transcriptase and cooling at 4° C., the device 500 for capturing nucleic acid in a single cell is allowed to move by the moving stage unit 604 such that the inlet 501 is arranged under the reagent-accommodating dispenser 611 that is filled with a 1×PBS buffer serving as a washing buffer. The reagent-accommodating dispenser 611 is pressurized by the dispensing pressurizer 612 at a certain pressure for a certain period of time, thereby introducing the 1×PBS buffer into the inlet 501. The 2nd syringe 608 was pulled to generate an orthogonal flow so as to wash the nucleic acid capture area 208 (FIG. 8 (b)).

The washed chip 100 for capturing nucleic acid in a single cell was removed from the device 500 for capturing nucleic acid in a single cell. The removed chip 100 was inserted in resin-made tubes (e.g., generally used tubes with a volume of 0.2 mL or 1.5 mL). An RNaseH solution prepared by mixing 1 µL of RNaseH (Invitrogen) and 1 µL of 10× RNaseH buffer (Invitrogen) was introduced into each tube and the tube was allowed to stand still at 37° C. for 30 minutes, thereby degrading mRNA (FIG. 8 (c)).

After mRNA degradation, 50 µL of a Tris-tween buffer (10 mM Tris-HCl, pH 8.0, 0.1% Tween solution) was introduced into the tube, and the chip 100 for capturing nucleic acid in a single cell was washed. A magnet was used for allowing only magnetic beads 205 to remain in the tube, followed by resuspension in 1 µL of the Tris-tween buffer. To each tube, 10 µL of a 2nd strand synthesis reagent prepared by mixing 1 µL of a 10× Platnum buffer, 1 µL of 2.5 mM dNTPs, 0.4 µL of 50 mM $MgSO_4$, 2.5 µL of each corresponding 10 µM gene-specific sequence primers, 0.1 µL of Platnum Taq H.F., and 5 µL of sterilized water was added. A reaction was conducted using a PCR apparatus at 98° C. for 10 seconds, 43° C. for 1 minute, and 68° C. for 3 minutes, thereby synthesizing a 2nd strand (FIG. 8 (d)). In this Example, as the gene-specific sequence primers, DNA probes having 20 types of sequences for genes (ATP5B, GAPDH, GUSB, HMBS, HPRT1, RPL4, RPLP1, RPS18, RPL13A, RPS20, ALDOA, B2M, EEF1G, SDHA, TBP, VIM, RPLP0, RPLP2, RPLP27, and OAZ1), to each of which a PCR amplification consensus sequence (Reverse) was added, were used. A sequence of 20±5 bases within 109±8 bases upstream of the poly-A tail of a target gene was used as the gene-specific sequence. A magnet was brought close to each tube at a storage temperature of 4° C. in which the 2nd strand was synthesized, thereby removing the 2nd strand synthesis reagent while exclusively allowing magnetic beads 205 to be left in the tube. Subsequently, the tube was maintained at 4° C. and brought again close to the magnet. In such state, the magnetic beads were washed twice with 50 µL of a Tris tween buffer. At the end, the beads were suspended in 1 µL of a Tris tween buffer. After the magnetic beads in the tube were washed, 14.3 µL of a PCR reagent prepared by mixing 7 µL of Gflex (TaKaRa), 2 µL of a primer having a PCR amplification consensus sequence (Forward), 2 µL of a primer having a PCR amplification consensus sequence (Reverse), 0.3 µL of Gflex polymerase (TaKaRa), and 3 µL of sterilized water was introduced into the tube. PCR amplification steps were conducted by maintaining each tube at 94° C. for 30 seconds, repeating the three-stage step of 94° C. for 30 seconds→55° C. for 30 seconds→68° C. for 30 seconds for 40 cycles, and maintaining the temperature at 68° C. for 3 minutes, followed by cooling at 4° C. (FIG. 8 (e)). As a result of these steps, target portions of the 20 types of target genes are amplified. Each PCR product has a substantially uniform size of 200±8 bases. After the PCR reaction, in order to remove a free PCR amplification consensus sequence primer or a residual reagent of an enzyme or the like in the solution, each amplified product resulting from amplification in the above steps was purified using PCR Purification (Qiagen) (FIG. 8 (f)). The purified solution was subjected to emPCR amplification or bridge amplification and then applied to a next-generation DNA sequencer of a manufacturer (e.g., Life Technologies (Solid/Ion Torrent) or Illumina (High Seq)) for analysis (FIG. 8 (g)).

In this Example, the steps after mRNA degradation (FIG. 8 (c)) were conducted by transferring the chip 100 for capturing nucleic acid in a single cell into a different tube. However, it is also possible to conduct steps until amplification by PCR reaction in FIG. 8 (e) in the device 500 for capturing nucleic acid in a single cell, collect a reaction solution from the device for capturing nucleic acid in a single cell, and conduct a reaction after purification of an amplified product in FIG. 8 (f) in a different tube.

According to this Example, it is possible to efficiently wash cells other than cells captured by the cell capture structure while maintaining high nucleic acid capture efficiency, thereby allowing the cell capture structure to prevent mRNA that is eluted upon cell lysis from flowing out in the surrounding area. Therefore, crosstalk can be reduced and analysis accuracy can be improved. In addition, since the number of cells captured by the cell capture holes can be counted, it is possible to exclusively use data of the reactors each capturing a single cell, thereby further improving analysis accuracy.

Example 3

Figure 9:
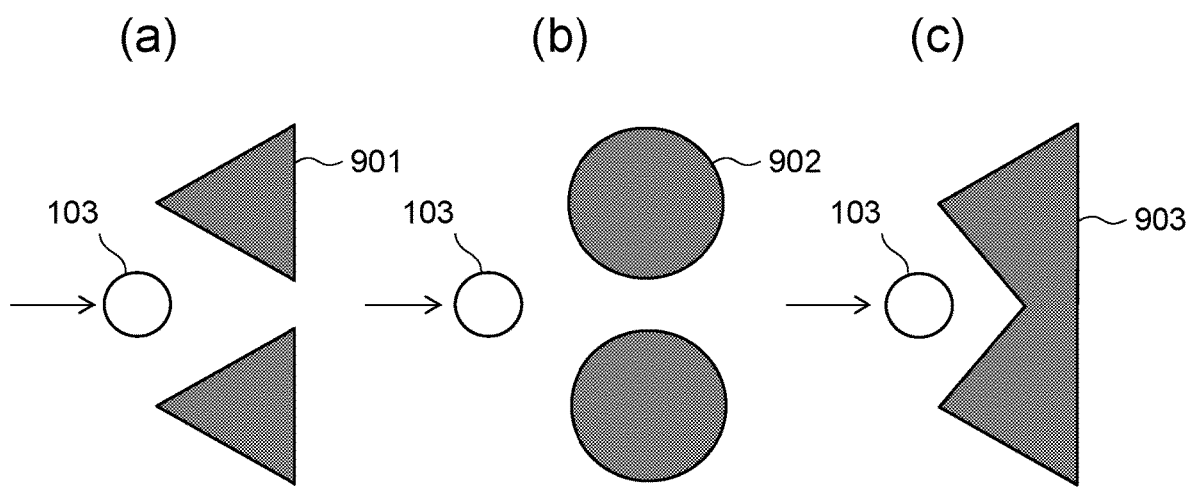
FIGS. 9($a$)-($c$) is a plan view of a cell capture structure.

In this Example, cell capture structures in various forms are described. FIG. 9 is a plan view of a cell capture structure different from the cell capture structure in the square U-shaped used in Example 1. Each arrow indicates the direction of a parallel flow to be generated upon cell capture.

Figure 10:
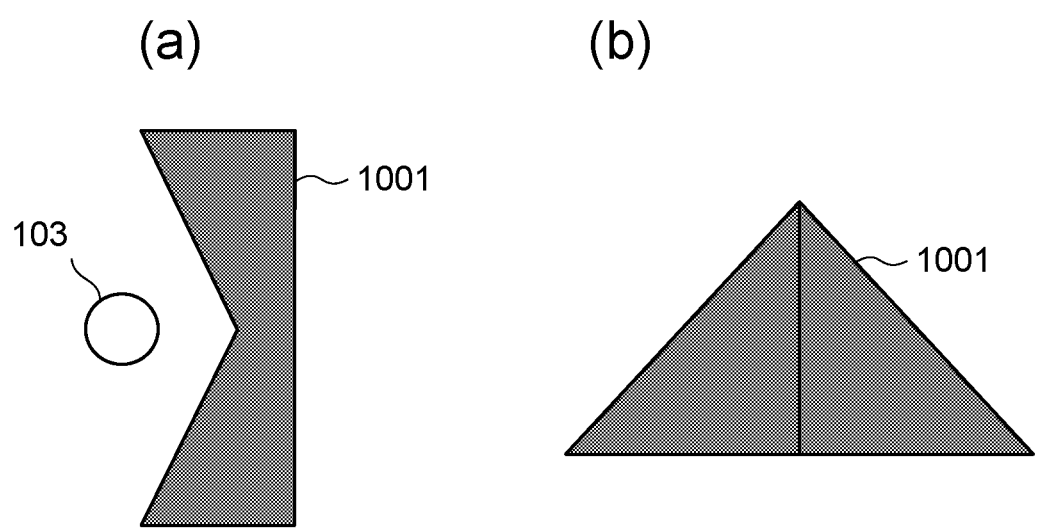
FIG. 10($a$) is a plan view of a cell capture structure.

A cell structure may be in the form of two triangular cylinders (FIG. 9 (a)) or circular cylinders (FIG. 9 (b)) arranged in parallel. It is necessary to set the height of each triangular cylinder or circular cylinder to not more than the height of two cells such that two or more cells are not captured. The height may desirably be about 10 to 15 µm. In addition, it may be preferable to set an interval between two cylinders to about 5 µm such that a cell does not pass between the two cylinders. Further, it may be desirable to set the total size of two cylinders in the direction vertical to the direction of the flow of a cell suspension to not more than the size of two cells such that a plurality of cells are not captured. The structure can be readily prepared using triangular cylinders or circular cylinders. The cell capture structure may not have a slit as illustrated in FIG. 9 (c). A cell capture structure 903 might prevent the flow of a cell suspension immediately above a cell capture hole 103, which may result in reduction of cell capture efficiency. Meanwhile, diffusion of mRNA upon elution of mRNA can be suppressed, thereby obtaining the effect of further reducing crosstalk. In addition to the cell capture structure illustrated in FIG. 9, a cell capture structure 1001, which has a triangular shape when viewed from the direction of the flow of a cell suspension as illustrated in FIG. 10, may be employed. It is necessary to set the height of the cell capture structure 1001 to not more than the height of two cells such that two or more cells are not captured. The height may desirably be about 10 to 15 µm. In addition, it may be desirable to set the size in the direction vertical to the direction of the flow of a cell suspension to not more than the size of two cells such that a plurality of cells are not captured. A cell capture structure may be structured as illustrated in FIG. 10. FIG. 10 (a) is a plan view of the structure. A cell suspension flows from left to right in FIG. 10 (a). FIG. 10 (b) is a front view of the structure viewed from the upstream of the flow of a cell suspension. In the case of the form of the above structure, cells are allowed to smoothly flow with the flow of a cell suspension if not being captured at the center of a triangle illustrated in FIG. 10 (b), thereby making it possible to prevent two or more cells from being captured.

In Example 1, the cell capture structure is integrated with the chip 100 for capturing nucleic acid in a single cell. Meanwhile, the cell capture structure may be formed immediately above the chip 100 for capturing nucleic acid in a single cell, for example, above a window 505. Accordingly, it becomes easy to produce a chip 100 for capturing nucleic acid in a single cell, which means that the cost can be reduced. In addition, the overall cost can be reduced by repeatedly using the device 500 for capturing nucleic acid in a single cell excluding the chip 100 for capturing nucleic acid in a single cell, or a window 505 alone.

Example 4

In this Example, a method for capturing a nucleic acid as a single-cell biomolecule from a sample comprising a plurality of cells using a device or system for capturing nucleic acid in a single cell, which adopts a mode of efficiently capturing cells in a cell suspension and conducting gene expression analysis at a single-cell level resolution is described.

Figure 11:
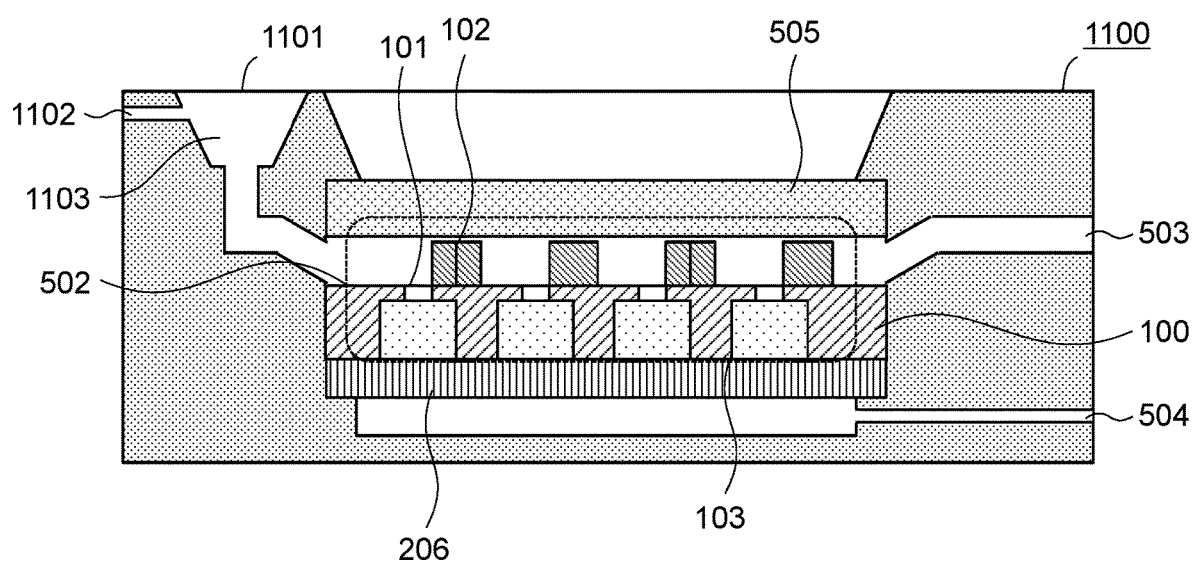
FIG. 11 is a schematic view of a device for capturing nucleic acid in a single cell.

FIG. 11 is a schematic view of a device 1100 for capturing nucleic acid in a single cell according to this Example. The basic configuration including the chip 100 for capturing nucleic acid in a single cell is the same as in Example 1. Only differences from Example 1 are described below. In the device for capturing nucleic acid in a single cell according to this Example, a 1st inlet 1101 and a 2nd inlet 1102 for introducing a cell suspension (sample), a reagent, and a washing buffer are connected to a solution storage area 1103 for temporarily storing a solution.

Figure 12:
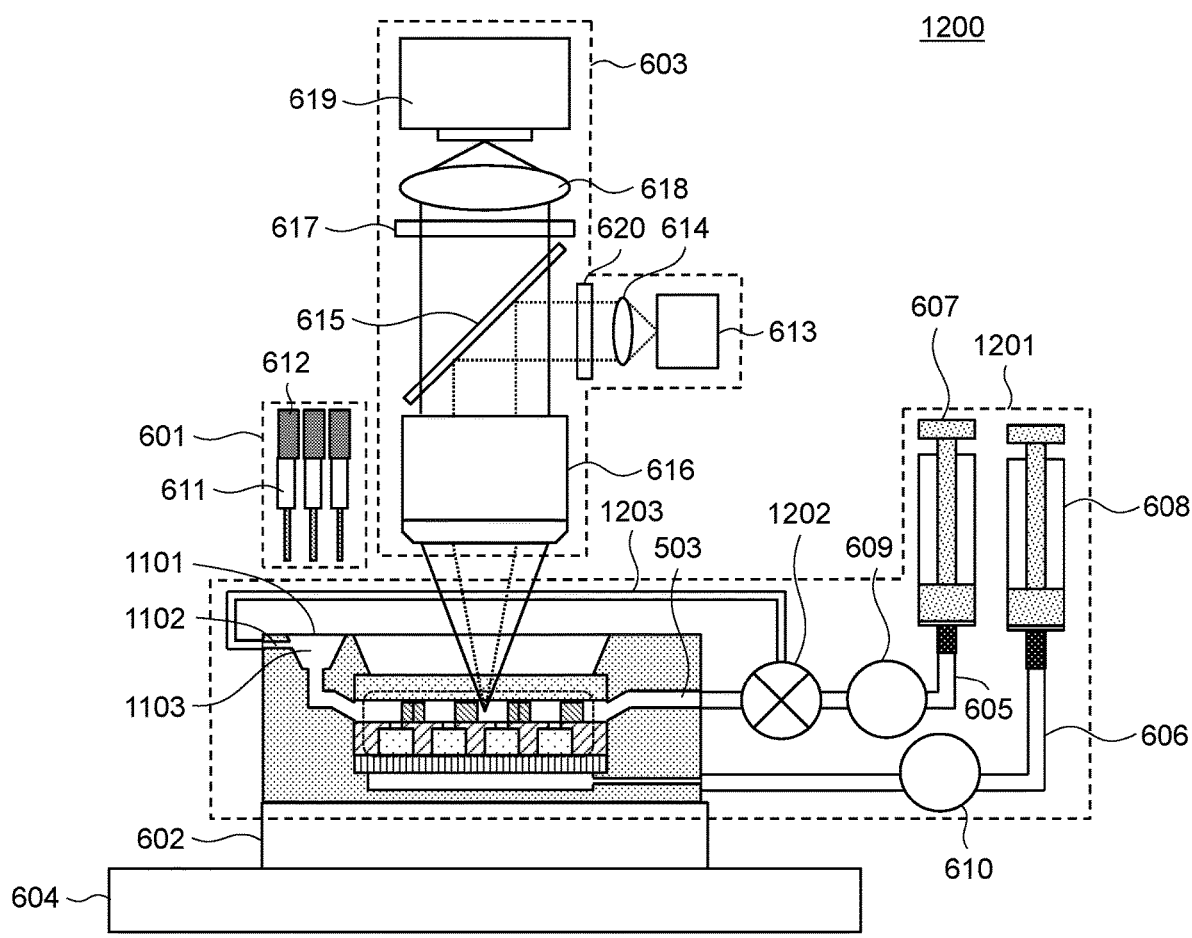
FIG. 12 is a schematic view of a system for capturing nucleic acid in a single cell.

FIG. 12 is a schematic view of a system 1200 for capturing nucleic acid in a single cell according to this Example. A system 1200 for capturing nucleic acid in a single cell is configured to comprise, in addition to the device for capturing nucleic acid in a single cell: a liquid feeding unit 1201; a reagent dispensing unit 601; a temperature control unit 602 for controlling the temperature of the device for capturing nucleic acid in a single cell; an optical observation unit 603 for optically observing the chip 100 for capturing nucleic acid in a single cell; and a moving stage unit 604 for allowing the device 1100 for capturing nucleic acid in a single cell to move to a desired position.

The liquid feeding unit 1201 is configured as described below. A three-way cock 1202 is connected to a 1st discharging tube 605 that is connected to a 1st outlet 503 of the device 1100 for capturing nucleic acid in a single cell. A liquid re-feeding tube 1203 is connected to one end of the three-way cock 1202. One end of the liquid re-feeding tube 1203 is connected to the 2nd inlet 1102 of the device 500 for capturing nucleic acid in a single cell. Other components, the reagent dispensing unit 601, the temperature control unit 602, the optical observation unit 603, and the moving stage unit 604 are the same as in Example 1.

Steps of cell capture are described below. A cell suspension was prepared by carefully washing about not more than 50 cells with 500 µL of 1×PBS so as not to damage the cells, removing PBS to a possible extent, and adding 100 µL of a 1×PBS buffer. GFP used as a phosphor has been incorporated into cells in advance. The device 1100 for capturing nucleic acid in a single cell is allowed to move by the moving stage unit 604 such that the 1st inlet 1101 is arranged under the reagent-accommodating dispenser 611 that is filled with a cell suspension. The reagent-accommodating dispenser 611 is pressurized by the dispensing pressurizer 612 at a certain pressure for a certain period of time, thereby introducing the cell suspension into a solution storage area 1103 from the inlet 1101. The 1st outlet 503 and the 1st syringe 607 are connected to form a flow channel via the three-way cock 1202. A syringe 607 is pulled to generate a parallel flow, thereby allowing a nucleic acid capture structure 102 on the chip 100 for capturing nucleic acid in a single cell to capture cells (FIG. 7 (a)). At such time, it is possible to generate an orthogonal flow by pulling a 2nd syringe 608. Note that the flow-rate of a parallel flow is adjusted to be greater than the flow rate of the orthogonal flow by the 1st and 2nd mass flow controllers 609 and 610. Next, the 1st syringe 607 and the liquid re-feeding tube 1203 are connected to form a flow channel via the three-way cock 1202. The syringe 607 is pushed, thereby introducing a cell suspension pushed by the syringe 607 into the solution storage area 1103 via the liquid re-feeding tube 1203. Thereafter, the 1st outlet 503 and the 1st syringe 607 are connected to form a flow channel via the three-way cock 1202. The syringe 607 is pulled to generate a parallel flow, thereby allowing the nucleic acid capture structure 102 on the chip 100 for capturing nucleic acid in a single cell to capture cells (FIG. 7 (a)). By repeating the above-described steps, it becomes possible to efficiently capture cells in a cell suspension by the cell capture structure. The steps of obtaining a gene expression profile by a next-generation (large-scale) sequencer following the above steps are the same as in Example 2.

All publications, patents and patent applications cited in the present description are incorporated herein by reference in their entirety.

REFERENCE SIGNS LIST

100 Chip for capturing nucleic acid in a single cell
101 Cell capture hole
102 Cell capture structure
103 Nucleic acid capture hole
104 Single-cell nucleic acid capture area
205 Magnetic beads
206 Porous sheet
207 Reactor
208 Nucleic acid capture area
309 Streptavidin
310 Biotin
311 DNA probe for capturing mRNA
412 PCR amplification consensus sequence (Forward)
413 Cell recognition tag sequence
414 Nucleic acid capture sequence
500 Device for capturing nucleic acid in a single cell
501 Inlet
502 Reaction field
503 1st outlet
504 2nd outlet
505 Window
600 System for capturing nucleic acid in a single cell
601 Reagent dispensing unit
602 Temperature control unit
603 Optical observation unit
604 Moving stage unit
605 1st discharging tube
606 2nd discharging tube
607 1st syringe
608 2nd syringe
609 1st mass flow controller
610 2nd mass flow controller
611 Reagent-accommodating dispenser
612 Dispensing pressurizer
613 Light source
614 Condenser lens
615 Dichroic mirror
616 Objective lens
617 Optical filter
618 Imaging lens
619 CCD camera
620 Optical filter
621 Liquid feeding unit
901 Cell capture structure
902 Cell capture structure
903 Cell capture structure
1001 Cell capture structure
1100 Device for capturing nucleic acid in a single cell
1101 1st inlet
1102 2nd inlet
1103 Solution storage area
1200 System for capturing nucleic acid in a single cell
1201 Liquid feeding unit
1202 Three-way cock
1203 Liquid re-feeding tube

The invention claimed is:

1. A system for capturing a biomolecule in a single cell, comprising:
a common inlet for serially introducing a sample, a washing buffer, and a cell lysis reagent into a flow channel;
a two-dimensional array having a plurality of single cell capture holes formed on one a surface of a substrate, and biomolecule capture areas inside of the substrate each comprising a biomolecule capture member for capturing the biomolecule extracted from individual cells which are respectively captured by the plurality of single cell capture holes;
the flow channel for flowing the sample, which comprises a plurality of cells to be assayed, from the common inlet and in a first direction in parallel with the surface of the substrate as a first flow;

a structure provided on the surface of the substrate so as to be opposed to the first direction on a downstream side of each of the plurality of single cell capture holes;

a first syringe connected via a first discharging tube to a first outlet;

a first mass flow controller capable of measuring and controlling a first flow volume of the first discharging tube, wherein the first mass flow controller controls a first flow rate of the first flow from the common inlet to the first outlet a second syringe connected via a second discharging tube to a second outlet;

a second mass flow controller capable of measuring and controlling a second flow volume of the second discharging tube, wherein the second mass flow controller controls a second flow rate of a second flow from the common inlet to the second outlet such that the first flow rate of the first flow is greater than that of the second flow rate of the second flow that is orthogonal to the first flow upon cell capture and the second flow rate of the second flow is greater than the first flow rate of the first flow upon biomolecule capture;

a reagent dispensing unit comprising a pressurizer and a set of reagent-accommodating dispensers;

a first-reagent-accommodating dispenser in the set of reagent-accommodating dispensers containing the sample and dispensing the sample into the common inlet;

a second-reagent-accommodating dispenser in the set of reagent-accommodating dispensers containing the washing buffer and dispensing the washing buffer into the common inlet;

a third-reagent-accommodating dispenser in the set of reagent-accommodating dispensers containing the cell lysis reagent and dispensing the cell lysis reagent into the common inlet; and an automatic moving stage unit for moving a position of the common inlet relative to the reagent dispensing unit, wherein a first position of the common inlet is associated with dispensing the sample, a second position is associated with dispensing the washing buffer, and a third position of the common inlet is associated with dispensing the cell lysis reagent.

2. The system according to claim 1, wherein the structure has a height of 20 μm or less and a width of 20 μm or less.

3. The system according to claim 1, which further comprises a return channel for returning, to the common inlet, the plurality of cells discharged via the first discharging tube.

4. The system according to claim 1, wherein the biomolecule is a nucleic acid.

5. The system according to claim 1, wherein the biomolecule capture member has a probe that specifically binds to the biomolecule.

6. The system according to claim 1, wherein the biomolecule capture member is a magnetic bead.

7. A method for capturing a biomolecule in each single cell from a sample comprising a plurality of cells, comprising:

providing a system for capturing the biomolecule, the system comprising:

a common inlet for serially introducing the sample, a washing buffer, and a cell lysis reagent into a flow channel;

a two-dimensional array having a plurality of single cell capture holes formed on a surface of a substrate, and biomolecule capture areas inside of the substrate each comprising a biomolecule capture member for capturing the biomolecule extracted from individual cells which are respectively captured by the plurality of single cell capture holes;

the flow channel for flowing the sample, which comprises the plurality of cells to be assayed, from the common inlet and in a first direction in parallel with the surface of the substrate as a first flow;

a structure provided on the surface of the substrate so as to be opposed to the first direction on a downstream side of each of the plurality of single cell capture holes;

a first syringe connected via a first discharging tube to a first outlet;

a first mass flow controller capable of measuring and controlling a first flow volume of the first discharging tube, wherein the first mass flow controller controls a first flow rate of the first flow from the common inlet to the first outlet;

a second syringe connected via a second discharging tube to a second outlet;

a second mass flow controller capable of measuring and controlling a second flow volume of the second discharging tube, wherein the second mass flow controller controls a second flow rate of a second flow from the common inlet to the second outlet such that the first flow rate of the first flow is greater than that of the second flow rate of the second flow that is orthogonal to the first flow upon cell capture and the second flow rate of the second flow is greater than the first flow rate of the first flow upon biomolecule capture;

a reagent dispensing unit comprising a pressurizer and a set of reagent-accommodating dispensers;

a first-reagent-accommodating dispenser in the set of reagent-accommodating dispensers containing the sample and dispensing the sample into the common inlet;

a second-reagent-accommodating dispenser in the set of reagent-accommodating dispensers containing the washing buffer and dispensing the washing buffer into the common inlet;

a third-reagent-accommodating dispenser in the set of reagent-accommodating dispensers containing the cell lysis reagent and dispensing the cell lysis reagent into the common inlet; and an automatic moving stage unit for moving a position of the common inlet relative to the reagent dispensing unit, wherein a first position of the common inlet is associated with dispensing the sample, a second position is associated with dispensing the washing buffer, and a third position of the common inlet is associated with dispensing the cell lysis reagent;

generating the first flow of the sample from the common inlet via the flow channel of the system to the first outlet;

capturing, based on the first flow of the sample, the individual cells by each of a set of single cell capture holes on the two-dimensional array;

washing the two-dimensional array by generating a third flow of the washing buffer, in parallel with the surface of the substrate, from the common inlet to the first outlet via the flow channel of the system lysing each captured cell by generating the second flow of the cell lysis reagent from the common inlet to the second outlet that is orthogonal to the one surface of the substrate; and capturing, based on the second flow of the cell lysis reagent, the biomolecule by each of a set of biomolecule capture members of the two-dimensional array.

8. The method according to claim 7, wherein the biomolecule is a nucleic acid.

9. A method for capturing a biomolecule in each single cell from a sample comprising a plurality of cells, comprising:
providing a system for capturing the biomolecule, the system comprising:
a common inlet for serially introducing the sample, a washing buffer, and a cell lysis reagent into a flow channel;
a two-dimensional array having a plurality of single cell capture holes formed on a surface of a substrate, and biomolecule capture areas inside of the substrate each comprising a biomolecule capture member for capturing the biomolecule extracted from individual cells which are respectively captured by the plurality of single cell capture holes;
the flow channel for flowing the sample, which comprises the plurality of cells to be assayed, from the common inlet and in a first direction in parallel with the surface of the substrate as a first flow;
a structure provided on the surface of the substrate so as to be opposed to the first direction on a downstream side of each of the plurality of single cell capture holes;
a first syringe connected via a first discharging tube to a first outlet;
a first mass flow controller capable of measuring and controlling a first flow volume of the first discharging tube, wherein the first mass flow controller controls a first flow rate of the first flow from the common inlet to the first outlet;
a second syringe connected via a second discharging tube to a second outlet;
a second mass flow controller capable of measuring and controlling a second flow volume of the second discharging tube, wherein the second mass flow controller controls a second flow rate of a second flow from the common inlet to the second outlet such that the first flow rate of the first flow is greater than that of the second flow rate of the second flow that is orthogonal to the first flow upon cell capture and the second flow rate of the second flow is greater than the first flow rate of the first flow upon biomolecule capture;
a reagent dispensing unit comprising a pressurizer and a set of reagent-accommodating dispensers;
a first-reagent-accommodating dispenser in the set of reagent-accommodating dispensers containing the sample and dispensing the sample into the common inlet;
a second-reagent-accommodating dispenser in the set of reagent-accommodating dispensers containing the washing buffer and dispensing the washing buffer into the common inlet;
a third-reagent-accommodating dispenser in the set of reagent-accommodating dispensers containing the cell lysis reagent and dispensing the cell lysis reagent into the common inlet; and
an automatic moving stage unit for moving a position of the common inlet relative to the reagent dispensing unit, wherein a first position of the common inlet is associated with dispensing the sample, a second position is associated with dispensing the washing buffer, and a third position of the common inlet is associated with dispensing the cell lysis reagent;
dispensing, while the automatic moving stage unit is at the first position, the sample into the common inlet from the first reagent-accommodating dispenser in the set of reagent-accommodating dispensers;
generating the first flow of the sample from the common inlet via the flow channel of the system to the first outlet;
capturing, based on the first flow of the sample, individual cells by each of a set of single cell capture holes on the two-dimensional array;
dispensing, from the second reagent-accommodating dispenser in the set of reagent-accommodating dispensers, the washing buffer into the common inlet while the automatic moving stage unit is at the second position;
washing the two-dimensional array by generating a third flow of a washing buffer, in parallel with the surface of the substrate, from the common inlet to the first outlet via the flow channel of the system;
dispensing, while the automatic moving stage unit is at the third position, the cell lysis reagent into the common inlet from the third reagent-accommodating dispenser in the set of reagent-accommodating dispensers;
lysing each captured cell by generating the second flow of the cell lysis reagent from the common inlet to the second outlet that is orthogonal to the surface of the substrate; and
capturing, based on the second flow of the cell lysis reagent, the biomolecule by each of a set of biomolecule capture members of the two-dimensional array.

* * * * *